US006407386B1

(12) United States Patent
Dotan et al.

(10) Patent No.: US 6,407,386 B1
(45) Date of Patent: Jun. 18, 2002

(54) SYSTEM AND METHOD FOR AUTOMATIC ANALYSIS OF DEFECT MATERIAL ON SEMICONDUCTORS

(75) Inventors: Noam Dotan, Givataim; Alexander Kadyshevitch, Modiin, both of (IL)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/255,495

(22) Filed: Feb. 23, 1999

(51) Int. Cl.$^7$ .......................... G01N 23/00; G21K 7/00
(52) U.S. Cl. ........................ 250/310; 250/311
(58) Field of Search ....................... 250/310, 311; 702/85, 86, 28, 30

(56) References Cited

U.S. PATENT DOCUMENTS 3,813,545 A * 5/1974 Barnhart et al. ............ 250/306
5,568,400 A * 10/1996 Stark et al. ................. 364/498
6,072,178 A * 6/2000 Mizuno ...................... 250/310

* cited by examiner

Primary Examiner—Jack Berman
Assistant Examiner—Kalimah Fernandez
(74) Attorney, Agent, or Firm—Sughrue, Mion, Zinn, MacPeak & Seas (57) ABSTRACT

A method and system for automatic EDX analysis of defects quantitatively take into consideration x-ray signals attributable to the background. The method and system are capable of automatically identifying suitable locations for background and defect x-ray sampling. The method and system are also capable of effectively and quantitatively, rather than qualitatively, removing signals attributable to the background and not the defect. One advantageous feature that enables the method and system to have a high throughput is termed "trace element analysis." The method and system are particularly beneficial for analysis of defects on semiconductor wafers and, due to automation, are suitable for in-line inspection of wafers in the fabrication plant.

16 Claims, 5 Drawing Sheets

SYSTEM AND METHOD FOR AUTOMATIC ANALYSIS OF DEFECT MATERIAL ON SEMICONDUCTORS

FIELD OF THE INVENTION

This invention relates to a system and a method for identifying the material composition of a sample by analysis of X-ray spectra emitted therefrom, and is most advantageous for identifying the material composition of defects found on semiconductor wafers.

BACKGROUND OF THE INVENTION

During the fabrication of devices on semiconductor wafers, the wafers undergo periodic inspection for defects. When such defects are discovered, it is important to identify the root-cause for the defects in order to correct the problem and avoid introducing similar defects to other wafers. However, it is prohibitively expensive to shut down the production line while a prolonged analysis of the root-cause is being performed. Therefore, the more information is gathered about the defect in the shortest time, the faster the root cause can be identified and the proper corrective actions can be implemented. One piece of important data which can help identify the root-cause is the composition of the material of the defect. Many attempts have been made in the art to obtain such identification.

One of the common techniques used in the microelectronics industry for analyzing the composition of materials is Energy Dispersive X-ray Spectroscopy (widely referred to as EDX or EDS) analysis. EDX analysis is generally performed using a Scanning Electron Microscope (SEM). The sample to be analyzed is irradiated by a primary beam of electrons, which causes x-ray emission from the sample's surface as the electrons of the atoms on and near the surface fall from their excited states to lower energy states. In general, the fundamental emissions, which are denoted as K, L and M-series are unique for each element. This provides a "finger print" which enables identification of the elements present on or near the surface of the sample. Both qualitative and quantitative analysis can be performed. The intensity of the x-ray signal is determined by a number of factors, such as the primary beam's energy, the detector's angle, the film thickness, the surface roughness and the concentration of the elements within the sample. The latest technology can detect elements from Be to U with high accuracy.

Wavelength-dispersive spectrometers (WDS or XRF) and EDX are also widely used in plasma research and various thin film and surface analysis. Examples of various x-ray material analysis systems include: Philips PW1400 wavelength dispersive X-ray fluorescence spectrometer; Rigaku RIX-3000; Kevex energy-dispersive X-ray fluorescence spectrometer; Voyager by Noran and Link by Oxford. For further informative reading, the reader is referred to U.S. Pat. Nos. 5,659,172; 5,118,041; 5,065,020; 4,988,872; and 4,382,183, the teachings of which are incorporated herein by reference.

As noted above, EDX analysis is used in the semiconductor industry, among others, to analyze the composition of defects on the wafers. An SEM system having EDX capabilities is exemplified in FIG. 1. An electron source 100 is activated to emit electrons, which are then formed into a primary electron beam 110 by lenses 120 and 130. Deflection coils 140 are used to direct and/or scan the beam onto the sample 150. The generated secondary electrons (SE) and the back-scattered electrons (BSE) are sensed by the electron detector 165, the output of which is used to generate an SEM image of the sample. Additionally, when the EDX system is activated, x-rays emitted from the sample 150 are detected by sensor 160, the signal of which is amplified by an amplifier 170 and sent to processor 180 for processing. The processor is connected in a known manner to a user interface 185 and memory 190. The output of the processor is provided in the form of a plotted spectrum 195.

Figure 1:
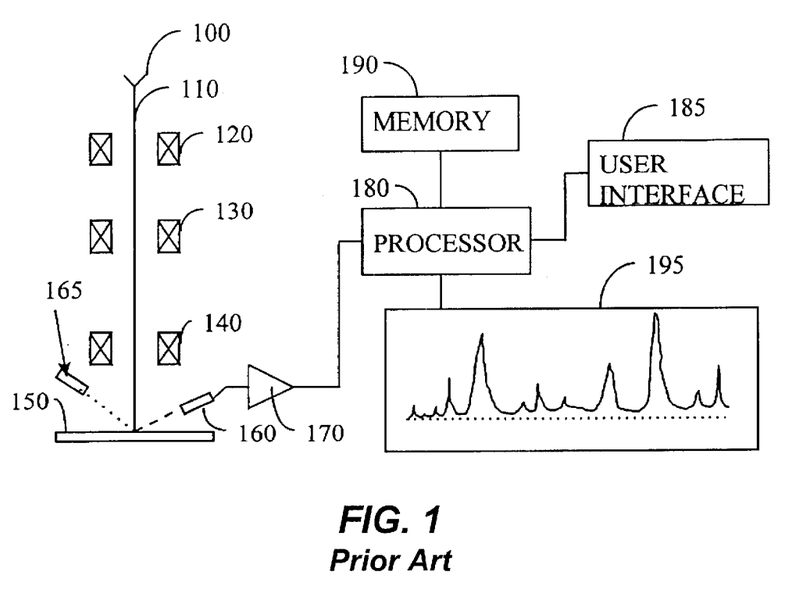
FIG. 1 depicts a conventional system for acquiring EDX signals and displaying the acquired spectra.

In examining a sample using the system exemplified in FIG. 1, the user directs the primary electron beam onto the detected defect and acquires the x-ray emission. The processor 180 then displays the spectrum 195 of the acquired X-ray emission, and the user analyzes the spectra peaks to obtain a list of the elements known to produce such peaks. However, this manual method is slow, cumbersome, and is affected by the fact that x-rays emitted from the defect include x-rays emitted from the background. Consequently, it is rendered hard, and sometimes impossible, to distinguish between the material of the defect and the material of the background, i.e., the wafer. This is particularly problematic in patterned wafers in which the top layer may include various elements which constitute the dielectric, metal lines, contact holes, etc.

In the prior art, it is attempted to overcome this difficulty by separately acquiring the x-ray spectra of the substrate and of the particle. In practice, the user has to manually point the primary beam to a selected location on the defect and a selected location on the background. The selection of the appropriate location is made by the user in reliance on his knowledge and experience. Then, the user qualitatively identifies spectra peaks that appear in both the background and the substrate, and decides based upon his experience whether to attribute each of such common element to the substrate. As can be seen, in addition to being slow, the results obtained from such a process can vary from operator to operator, depending on their knowledge and experience. Thus, there's a need in the prior art for a system which automatically investigates the defect and the background spectra to correctly identify the material constituting the defect.

SUMMARY OF THE INVENTION

The present invention provides a system for automatic EDX analysis of defects, quantitatively taking into consideration x-ray signal attributable to the background. The system is particularly beneficial for analysis of defects on semiconductor wafers and, due to its automation, is suitable for in-line inspection of wafers in the fabrication plant.

One advantageous feature that enables the system to have a high throughput is termed "trace element analysis." As is known, basically two types of particle defects can be present on a wafer: one type is a leftover processing material, such as a particle left from etching, a photoresist residue, etc. The other type is "foreign" particles, i.e., particles introduced from external sources, such as the processing chamber's walls, the chuck holding the wafer, vacuum and gas lines, etc. In production-line monitoring, it is very important to rapidly identify foreign particles since they indicate that a processing chamber is failing and requires repair or service. Accordingly, in the trace element analysis the system analyzes the x-ray spectra obtained and, if an element that under no circumstances should be present on a wafer is noted, such as iron for example, the system immediately issues an alarm that a foreign particle has been introduced. This helps focus the yield engineer to investigate problems relating to the equipment and not the process.

Another advantageous feature of the invention is its ability to automatically perform EDX analysis of defects, taking into consideration x-ray signal attributable to the background. Specifically, the system is capable of automatically identifying suitable locations for background and defect x-ray sampling. The system is also capable of effectively and quantitatively, rather than qualitatively, remove signals attributable to the background and not the defect.

The general steps of the inventive method include (not necessarily in that order):

1—detecting the defect;
2—analyzing the image of the defect and its surroundings;
3—determining the preferred point on the defect for the defect EDX spectrum acquisition, and acquiring the EDX spectrum of the defect;
4—analyzing the defect spectrum and performing the simple trace element analysis;
5—either determining the preferred point on the substrate for the substrate EDX spectrum acquisition and acquiring an x-ray spectra from the preferred point, or;
6—comparatively analyzing the defect and background spectra to yield a net defect spectrum identifying the composition of the defect material;
7—comparing the net spectrum to the spectra in a defect material spectrum library to identify the nature and source of the defect.

BRIEF DESCRIPTION OF THE DRAWINGS

Other features and advantages will become apparent from the following detailed description of the preferred embodiments, referencing the various Figures, in which:

FIG. 3a depicts a section of a wafer having two layers of different material thereupon, while

FIGS. 6a–6d are spectra counts of various defects obtain by a system according to the invention, while FIGS. 7a–7d are net spectra counts obtained from the spectra counts of FIGS. 6a–6d, while

DETAILED DESCRIPTION OF PREFERRED EMBODIMENTS

Figure 2:
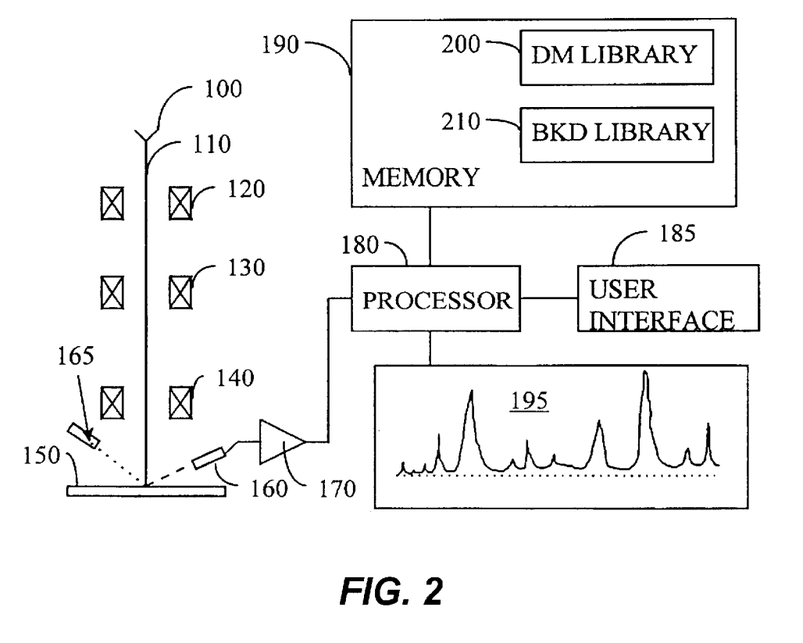
FIG. 2 depicts an EDX system according to an embodiment of the invention.

FIG. 2 exemplifies an EDX system according to an embodiment of the present invention. Elements in FIG. 2 which are the same or similar to those in FIG. 1 are identified with the same characters. A noticeable distinction in the system of FIG. 2 is the addition of a defect material library 200 and a background material library 210. While the libraries are indicated inside memory 190, they may reside in a different memory of the system, or may be a remote memory accessible by the system via the plant's network, or any other means.

The libraries are basically memory areas and may or may not have pre-loaded data. More specifically, the defect material library 200 includes spectral data relating to materials that generally constitute defects. For example, such material may be various photoresists used in the industry or various metals used for lines and contact holes. The defect library may or may not include data relating to "foreign matter" defects. When data related to "foreign matter" defects is included, it is preferably segregated from the other defect material data and preferably includes data relating to the possible sources of such foreign material (e.g., chamber walls for metals and vacuum lines for organic material). The background material library 210 contains spectral data relating to the various layers on the wafer which may constitute the background when the defect image is acquired. The background data can be pre-loaded, obtained during the set-up procedure, or acquired during the normal operation of the system. The processor 180 advantageously uses the libraries, as explained further below, to automatically isolate the spectra of the defect from the background and properly identify the defect's material composition.

In the preferred embodiment, the background and defect images are acquired by an SEM capable of collecting SE and/or BSE electrons from different angular sectors, thereby generating images from multiple perspectives. This type of SEM enables high resolution imaging of various topographic features. Such an SEM is described in U.S. Pat. Nos. 5,644,132 and 4,941,980, the entire disclosures of which are incorporated herein by reference. However, it should be appreciated that the invention can be implemented with any other system capable of imaging the sample, and causing an x-ray emission from the sample.

Figure 3A:
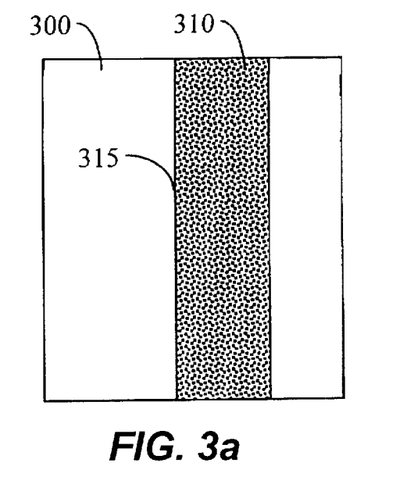
Figure 3B:
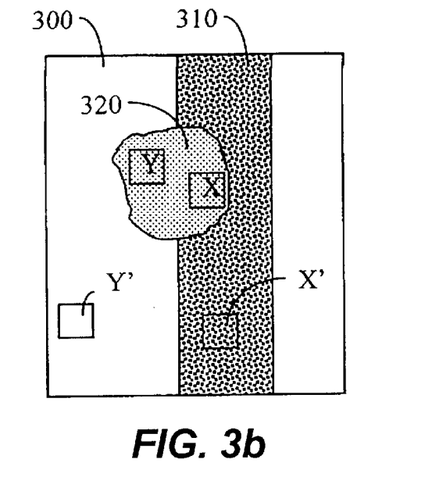
FIG. 3b depicts a corresponding location on the wafer but having a particle thereupon.

Before commencing the material analysis, the system of FIG. 2 performs preliminary operations, as will be discussed with reference to FIGS. 3a and 3b. Specifically, FIG. 3a depicts an image of a certain location on the wafer, while FIG. 3b depicts an image of a similar location, but having a defect thereupon. The location of FIG. 3b may be a different die (especially for logic devices) or a different cell (especially for memory devices) than that of FIG. 3a, but its coordinates within the die or cell are similar to that of FIG. 3a. The surface of the location depicted comprises a insulator material 300 (e.g., dielectric) and a line feature 310 (e.g., deposited metal or ion implanted line), which are of different composition. The defect material 320, is of yet another composition.

The first task the system of FIG. 2 has to accomplish is to re-detect the defect, and then isolate it from the rest of the image. That is, when a wafer is loaded onto the system, a defect map is also loaded onto the system. A defect map is produced by conventional techniques, such as by scanning the surface of the wafer with a high-speed inspection tool (a CCD, a laser or an SEM may be employed for this purpose). Then using statistical methods, typically involving algorithms and/or gray-scale analysis, the inspection tool identifies suspected locations on the wafer having a high probability of having a defect. The output of such an inspection tool is generally referred to as a defect map. So, when a wafer is transferred from the inspection system to a defect review system, its corresponding defect map is also transferred.

However, since the field of view of a defect review SEM system is generally smaller than that of an optical system, and its resolution is more than an order of magnitude better, the coordinates provided in the defect map frequently do not translate to accurate positioning of the SEM's primary beam over the defect. Thus a procedure has to be followed to "re-detect" each defect designated in the defect map. Although any known re-detection procedure would suffice, the preferred method is that described in the above cited U.S. Pat. No. 5,659,172.

Once the defect has been re-detected and a SEM image of it and a reference area has been obtained—e.g., as depicted in FIGS. 3a and 3b—the system performs a "defect boundary" analysis. This is done by comparing the images of FIGS. 3a and 3b and determining which edge boundaries are present in FIG. 3b, but absent in FIG. 3a. The defect boundary analysis provides a defect footprint, i.e., a contour boundary of the defect which is in essence a boundary curve drawn around the defect which includes only the defect. Thereafter, the system is basically ready to begin the material analysis, which can be done in various ways, as will be described below.

As depicted in FIG. 3b, the defect may lie on a background comprising more than one material, e.g., two are depicted in the Figures. Therefore, the system next selects a sampling location which lies over only one material. This may be, for example, either the location marked X or the location marked Y in FIG. 3b. If desired, both locations can be chosen and the analysis can be performed for each location. The system then acquires two spectra: one at the chosen defect location, and one at a clear location of the background material, e.g., the locations marked X' and Y'.

The selection of the preferred point on the defect for the EDX sampling can be done in various manners, including by geometrical considerations. For example, if the defect lies on a single background material, the preferred point can be the center of the defect, i.e. the point on the defect which is further away from an defect boundaries. This can be defines as, for example, the mid-point of the major axis of the defect, the mid-point of the minor axis of the defect, the crossing point of the major and minor axes of the defect (provided it is within the defect boundaries) etc.

If the particle resides on the boundary of two or more structure features, the defect footprint may first be divided into corresponding regions. This can be done, e.g., by noting the boundary line in the reference image that is missing from the defect image. In the example, a section of boundary line 315 of FIG. 3a is missing in FIG. 3b. This section of the boundary line can be used to divide the defect footprint to a section laying over insulator 300 and a section lying on line feature 310. Then, if one wishes to perform the analysis only once, i.e., with respect to only one background material, the system may first determine which section of the divided defect footprint is larger. The "center" determination exemplified above can then be applied to the chosen section.

Additionally, it should be appreciated that the selection of the actual point to sample the defect may be the entire defect. That is, one can illuminated the entire general area of the defect and sample the x-ray signal obtained therefrom. This may be especially the case where the defect's size is on the order of the primary beam's diameter.

The background spectra used for the proceeding analysis can generally be obtained from the following sources:

I—Sampling all the possible backgrounds in advance, and storing the obtained specta in the background library 210. Then appropriate data can be fetched according to the position of the defect on the background per the boundary analysis.

II—Acquiring a spectrum outside the defect's geometrical area according to the defect boundary analysis.

III—Acquiring a spectrum of a large area around the defect, the area being sufficiently large so that the defect weight will be negligible and the acquired spectrum will represent the background underneath the defect.

IV—Acquiring spectrum in a reference die at the same position of the defect.

Figure 4A:
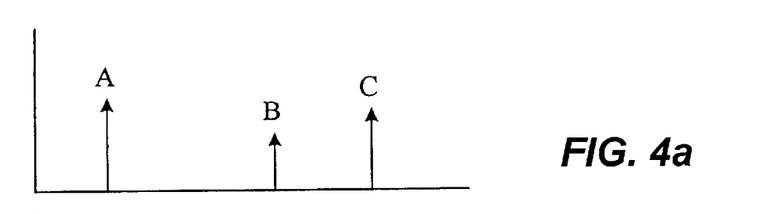
FIGS. 4a–4d depict various spectra count numbers useful for exemplifying the present invention.

The system then performs a quantitative analysis of the defect and background spectra, to obtain the net count numbers of the different elements present in the spectra and the background. The system then has three sets of data available to it as shown in FIGS. 4a–4d: count numbers of the defect materials for the various entries in the defect library (one entry is shown in FIG. 4a and another in FIG. 4d); count numbers of the background spectra (FIG. 4b); and count numbers of the defect spectra (FIG. 4c). Note that in FIGS. 4a–4c a single prime designates the count number of that element in the background spectra, and a double prime designates the count number of that element in the defect spectra.

Figure 4B:
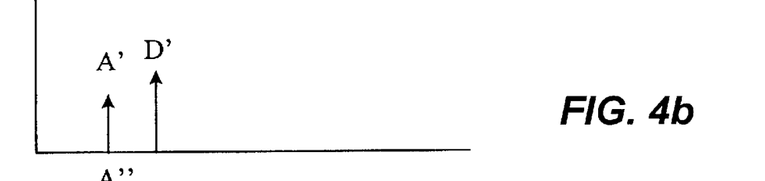
Figure 4C:
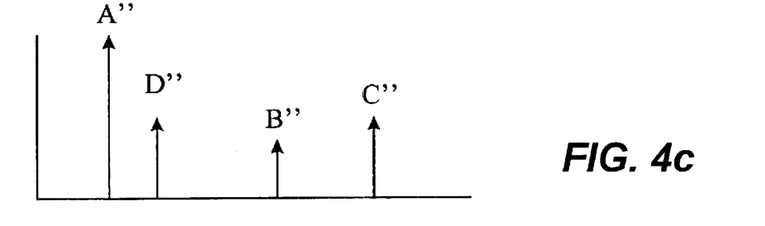

Then, a list of the elements that are present in both the defect and background spectra is generated (e.g., for FIGS. 4a–4c it would be elements A and D). For each element in the list, a ratio of its net count in the defect spectra to the net count in the background spectra is calculated (e.g., A"/A' and D"/D'). It is then assumed that the element having the smallest ratio is an element which is not present in the defect, i.e., its spectra is attributable solely to the background material (hereinafter, this element would be referred to as a "non-present element" or "NPE"). From the example of FIGS. 4a–4c, it can be seen that the ratio D"/D' would be smaller than that of A"/A'. However, it should be appreciated that other algorithms may be used. For example, a NPE ratio may be set, so that only if the smallest ratio exceeds the NPE ratio it is considered as a non-present element. If no NPE is found, the system may then proceed to the comparison stage and skip the normalization stage.

According to the preferred embodiment, the proceeding steps are performed under the assumption that the acquired spectrum at the chosen location is a linear combination of x-ray emitted from the defect material and the background material under the defect. While this assumption simplifies the process for fast analysis, relationships other than linear may be used. Specifically, since a linear relationship is assumed, the background spectra is normalized according to the count of the element which was determined not to be present in the defect. This normalization can be linear per the preferred embodiment, or otherwise if chosen. The resulting normalized background spectra is then subtracted from the defect spectra to obtain a net defect spectra. In the example of FIGS. 4a–c: A"–$\underline{A}$', where $\underline{A}$' designated the count number of A' normalized by the count number of D'. The net defect spectra is then compared to the defect material library 200 to determine the nature of the defect, e.g., left over resist material.

A numerical example is provided herein for further clarification of the invention. A defect spectrum and a background spectrum are obtained. In both spectra elements O and Si are present among other elements, with the following counts: In the defect spectrum: O—1000 net counts, Si—500 net counts In the background spectrum: O—10000 net counts, Si—10000 net counts The defect/background spectra ratios are 0.1 for O and 0.05 for Si, and therefore Si is designated as the non-present element (i.e., having the smaller ratio). The background spectrum is then normalized according to the non-present element Si net count number in the defect spectrum. In this numerical this example, the background spectrum is normalized to have 500 net counts in the Si line (i.e., the background spectrum count is divided by 20). The normalized background is then subtracted from the defect spectrum so that Si is removed from the defect spectrum, and O is adjusted correspondingly.

Of course, the assumption that the element having the smallest ratio is not present in the defect material may not hold true. There are possible cases where some or all of the elements that appear in the background spectrum are present in the defect material. Therefore, the system may also perform the following procedure. First, the defect material library is scanned for those defect materials which include the element considered non-present, and a collection of those hits is obtained. Then, for each hit from the collection, the system normalizes the background spectra according to the net count of the "not present" element in that hit, and subtracts the normalized background spectra from the hit (i.e., so that the "non present" element would be removed from the hit). Then the system compares the net defect spectra to the hits that were normalized in this manner. The hits that do not include the non-present element are compared to the net defect spectrum without any preliminary processing. In general, the comparison can be based on the least square method or any other algorithm.

Figure 4D:
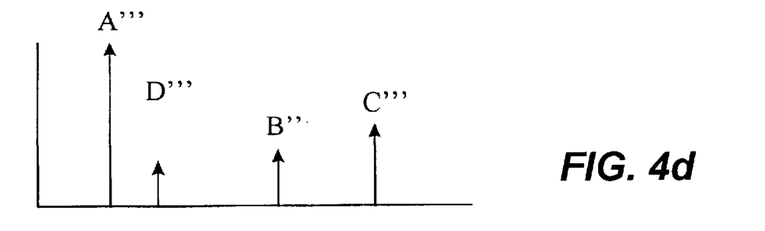

For example, assuming that from the defect material library 200 the system obtains a hit having the defect material data as exemplified in FIG. 4d, which includes a certain among of element D (triple prime indicating that the element appears in one of the hits obtained from the defect material library). The background spectra is then normalized according to D''', so that when the normalized background spectra is subtracted from the hit spectra, D''' will be deleted from the hit spectra. The hit net spectra is then compared to the net defect spectra to identify the nature of the defect material.

A particularly advantageous feature of the invention will now be described, which is referred to herein as the "trace element analysis." In many cases, the presence of some specific element (or few elements) in the defect spectrum determines the defect material or suggests its source. For example, no iron (Fe) is used in the fabrication of semiconductor devices. The detection of any amount of such element on the defect spectra suggests immediately that it was introduced from an external source, and is probably not a result of defective fabrication exact recipe. Therefore it is advantageous to flag such a defect immediately. This is done using the inventive trace element analysis.

For the trace element analysis the procedure is rather simplified and rapid. Specifically, an x-ray spectra is collected from any chosen location on the defect and analyzed for its composition. If the spectra includes traces of any element combination which is included in the foreign matter defect library, the defect is flagged as being caused an external source and a list of potential causes for that foreign material is fetched from the foreign material library. If a foreign material library is not used, the defect is flagged as being caused by an external source if the collected spectra includes traces of an element which is not listed in any of libraries 200 and 210.

Figure 5:
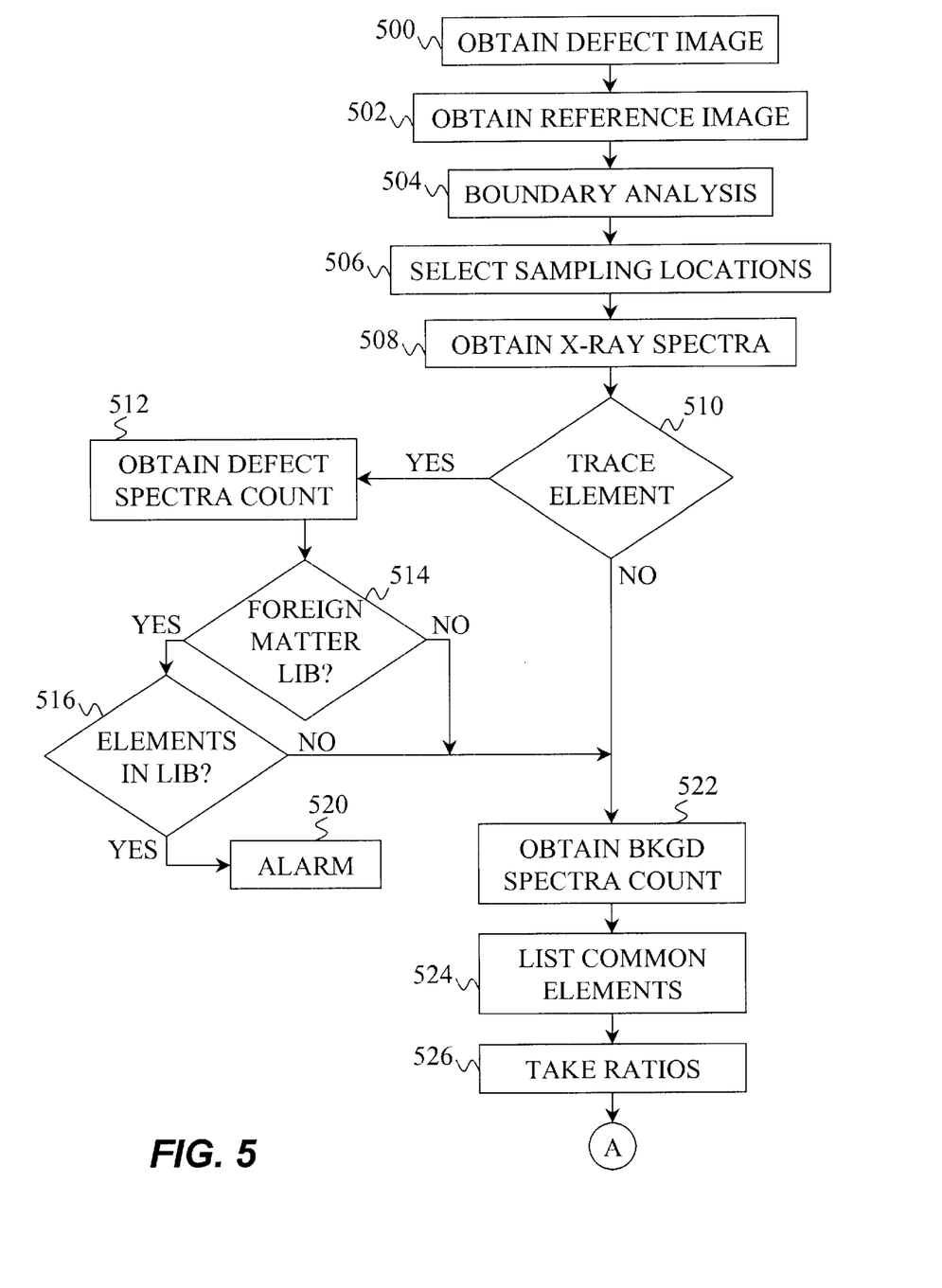
FIG. 5 is a flow chart exemplifying the preferred embodiment of the invention.

An exemplary flow chart for carrying out the invention is provided in FIG. 5. A defect and reference images are obtained in steps 500 and 502, and a boundary analysis is performed at step 504. A sampling location is then selected, step 506, and an x-ray sampling is collected at step 508. If a trace element analysis is to be performed (junction 510), the process proceeds to step 512. Otherwise, it proceeds to step 522.

In step 512 count numbers of the defect spectrum is obtained to determine the elements present in the spectrum sample. If a foreign matter library exists (junction 514), it is determined whether any of the elements combination from the spectra sample matches an element from the library (junction 516). If so, an alarm is issued. Additionally, if the foreign element library includes data regarding possible sources of that element, the data is made available to the user. If all the elements from the sample do not fit any defect matter library element, the process continues to step 522.

In step 522 count numbers of the background spectra is obtained, and in step 524 a list of the common elements, i.e., elements that appear in both the defect and background spectra, is made. In step 526 the ratios of all the common elements from the defect and the background are obtained, and in step 528 the element corresponding to the smallest ratio is selected as the NPE. In step 530 the background spectra is normalized per the NPE and, in step 532, the normalized background spectra is subtracted from the defect spectra. The system then searches the defect material library to find the best match. For each hit, the system checks whether it contains the NPE (junction 536). If so, the system normalizes the hit to remove the NPE from the hit spectra count (step 538) and then compares it to the net defect spectra count (step 544). If the hit does not contain NPE, it is compared to the net defect spectra count without normalization. To exhaust all the hits, a loop (steps 546, 550) is provided. When all the hits have been exhausted, the best hit is then provided as the defect material, together with any other information available from the defect material library (step 548).

It should be appreciated that the embodiments described above are exemplary, and the invention is not limited to such implementation. To the contrary, various variations and modifications may be made without departing from the scope and spirit of the invention, as defined in the appended claims.

For example, in various circumstances, the material composition of the background will be known beforehand. One simple such example is when inspecting bare or non-patterned wafers. If the wafer is a "bare wafer", it is basically a substrate of known composition, i.e., silicon. Thus, any element detected other than silicon comprises a defect. Similarly, if the wafer is a "non-patterned" wafer, for example, monitoring wafers, the material composition of the top uniform layer is known, e.g., a $SiO_2$ dielectric. Under such circumstances, there is no need to sample the spectra on the background. Instead, one can store a collection of such material spectra in the background library 210, and when the background spectra is needed for computation and analysis, the processor 180 fetches that spectra from the library 210.

Of course, the above-noted process is not limited to bare or non-patterned wafers, but can be used anytime the background composition is known beforehand. Thus, for example, the system can be programmed so that during the set-up process (e.g., recipe preparation), the user takes spectra sampling of selected locations on the wafer corresponding to the various different materials present on the top layer. The system then compares each sample to the background library and determine the material constituting the background. Once a list of the materials present on the wafer on the various background locations is obtained, the system need not sample the background spectra anymore. Instead, it fetches the data required for computation and analysis from the background library 210.

Another useful modification is as follows. Whenever the background library 210 contains no data, or contains no data pertaining to the specific layer to be inspected, the system can create or update the background library during the set-up procedure. Specifically, the system samples the spectra on various locations on the wafer, corresponding to the different material present on the layer under investigation. The spectra is analyzed for count numbers, and stored in the background library 210. Thereafter, whenever the processor 180 requires background data for computation or analysis, it fetches the background data from the library 210.

Figure 6A:
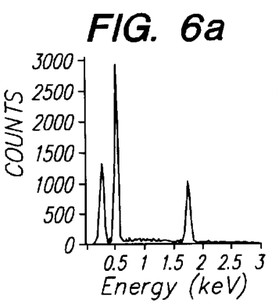
Figure 6B:
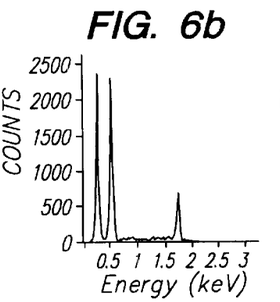
Figure 6C:
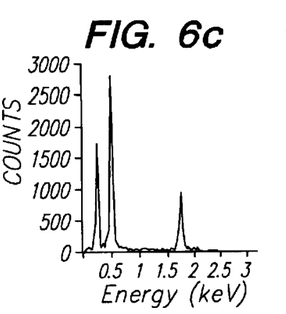
Figure 6D:
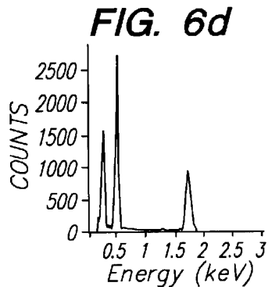
Figure 6E:
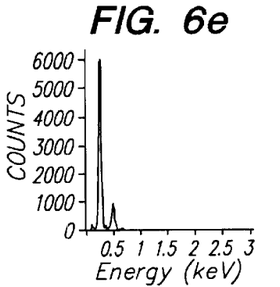
FIG. 6e is a spectrum count of a photoresist.
Figure 7A:
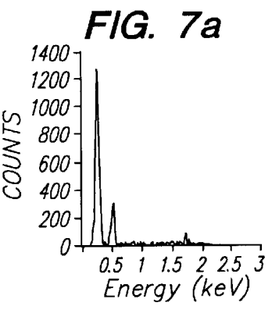
Figure 7B:
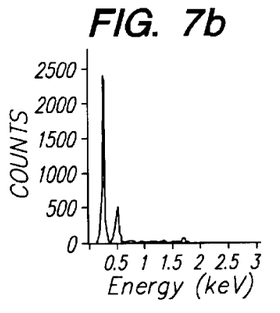
Figure 7C:
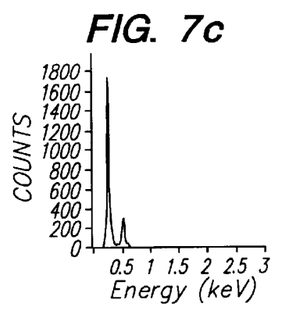
Figure 7D:
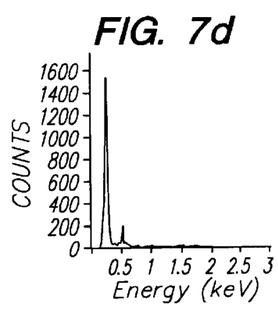
Figure 7E:
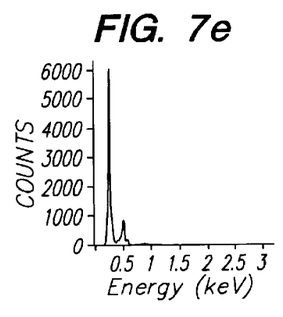
FIG. 7e is the same as FIG. 6e.

A system according to the above described preferred embodiment was used to investigate defects on a semiconductor wafer. FIGS. 6a–6d depict four x-ray spectra obtained from four defects found on the wafer, specifically, from a silicon oxide layer. (The energy is plotted along the x-axis, while the count is plotted along the y-axis.) FIG. 6e depicts a spectrum obtained from a photoresist, i.e., a spectrum acquired for storage in the defect material library. As can be seen, all the spectra of FIGS. 6a–6d include a peak at about 1.74 keV; however, the spectra of FIG. 6e does not include such a peak. Thus, using a simple search in the defect library would not result in a probable hit.

FIGS. 7a–7d depict the net defect spectra of FIGS. 6a–7d. That is, a background spectra was obtained, ratios of common elements were taken which resulted in silicon as being the common element and therefore selected as the NPE, and the normalized background spectra was subtracted from each of the spectra of FIGS. 6a–6d, resulting in the spectra of FIGS. 7a–7d. As can be seen, the peak at 1.7 keV was eliminated and, thus, a clear match to photoresist (FIG. 7e) can be obtained. Consequently, the system identified the defects as being photoresist residue.

As demonstrated above, the inventive system has beneficial advantages for material analysis, especially material analysis of defects residing on semiconductor wafers. It would be appreciated that the system can improve any material analysis of an object, especially when such object is situated on a background so that the collected spectra may include elements of the background.

What is claimed is:

1. A method for automatic material analysis of an object within a background, comprising the steps of:

automatically determining a desired location on the object for spectrum acquisition;

acquiring an object spectrum in accordance with said determining;

obtaining a background spectrum;

obtaining count numbers from the object spectrum, corresponding to elements present in the object;

obtaining count numbers from the background spectrum, corresponding to elements present in the background;

analyzing the count numbers of the object spectrum to determine whether a count number appearing in the object spectrum is a non-present element in the object;

analyzing the count numbers of the background spectrum to determine whether a count number appearing in the background spectrum is a non-present element in the background;

standardizing the spectra count of the object according to the count of said non-present element to obtain a net object count; and analyzing the net object count to determine the material composition of the object.

2. The method according to claim 1, wherein the step of analyzing comprises:

determining all common elements that appear in the count spectra of the background and object;

for each common element calculating a count ratio of object count to the background count for that element;

analyzing the ratios to determine whether any of the common elements is a non-present element.

3. The method of claim 2, wherein the step of analyzing the ratios comprises defining the element having the smallest ratio as the non-present element.

4. The method of claim 2, wherein the step of analyzing the ratios comprises selecting the smallest ratio and, if the smallest ratio exceeds a predetermined threshold, defining the element corresponding to the smallest ratio as a non-present element.

5. The method of claim 1, wherein the step of automatically determining comprises:

obtaining an image of the object;

performing a boundary analysis to obtain an object footprint; and, selecting a point on the object footprint from spectra measurement.

6. The method according to claim 1, wherein the step of standardizing comprises the steps of:

normalizing the spectra count of the background according to the count number of the non-present element to obtain a normalized background; and subtracting the normalized background from the object spectra count of the object to obtain said net object count.

7. The method of claim 1, wherein the step of analyzing the net object count comprises comparing the net object count to an object material library.

8. The method of claim 6, wherein the step of analyzing the net object count comprises comparing the net object count to an object material library.

9. The method of claim 1, wherein the step of obtaining a background spectrum is performed by one of the method:

fetching a background spectrum from a memory;

acquiring a background spectrum from a selected point on the background; and acquiring a background spectrum from a large background area near the object.

10. The method of claim 8, further comprising the steps of:

for each entry in the object material library determining whether the entry contains the non-present element; and if the entry contains the non-present element, normalizing the entry to remove the non-present element.

11. The method of claim 10, wherein the step normalizing the entry comprises reducing the level of all count of that entry by an amount corresponding to the count of the non-present element in that entry.

12. The method of claim 1, further comprising the steps of:

comparing each count number of the object spectra count to a list of elements in an object material library; and if none of the count numbers of the object spectra count appears in the list of elements in the object material library, then defining said object as a foreign object.

13. The method of claim 1, further comprising the steps of:

comparing each element of the object spectra count to a list of elements in a foreign object library; and, if one of the elements of the object spectra count appears in the list of elements in the foreign object library, defining said object as a foreign object.

14. A method for automatic material analysis of an object within a background, comprising the steps of:

automatically determining a desired location on the object for spectrum acquisition;

acquiring an object spectrum in accordance with said determining;

obtaining count numbers from the object spectrum, corresponding to elements present in the object;

obtaining count numbers from the background spectrum, corresponding to elements present in the background;

comparing each count number of the object spectrum count to a list of elements in a material library;

comparing each count number of the background spectrum count to a list of elements in a material library; and if none of the count numbers of the object or background spectrum count appears in the list of elements in the material library, then defining said object as a foreign object.

15. A method for automatic material analysis of an object within a background, comprising the steps of:

automatically determining a desired location on the object for spectrum acquisition;

acquiring an object spectrum in accordance with said determining;

obtaining count numbers from the object spectrum, corresponding to elements present in the object;

obtaining count numbers from the background spectrum, corresponding to elements present in the background;

comparing each count number of the object spectrum count to a list of elements in a foreign object library;

comparing each count number of the background spectrum count to a list of elements in an foreign object library; and if any of the count numbers of the object or background spectrum count appears in the list of elements in the foreign object library, then defining said count number as a foreign object.

16. A system for material analysis of defects on substrates, said system comprising:

an energized beam for causing said substrate to emit X-rays from one or more automatically selected locations on the substrate;

an X-ray detector collecting X-rays emitted from the substrate;

a processor receiving and analyzing the output of the X-ray detector;

a library containing substrate defect information; and a library containing materials information.

* * * * *